(12) United States Patent
Deneuvillers (10) Patent No.: US 10,433,878 B2
(45) Date of Patent: Oct. 8, 2019

(54) IMPLANTABLE DEVICE, IN PARTICULAR FOR CORRECTING AT LEAST ONE VERTEBRAL LEVEL

(71) Applicant: COUSIN BIOTECH, Wervicq Sud (FR)

(72) Inventor: Guy Deneuvillers, Merlimont (FR)

(73) Assignee: COUSIN BIOTECH, Wervicq (FR)

( * ) Notice: Subject to any disclaimer, the term of this patent is extended or adjusted under 35 U.S.C. 154(b) by 0 days.

(21) Appl. No.: 14/904,987

(22) PCT Filed: Jul. 11, 2014

(86) PCT No.: PCT/FR2014/051801
§ 371 (c)(1),
(2) Date: Jan. 14, 2016

(87) PCT Pub. No.: WO2015/007985
PCT Pub. Date: Jan. 22, 2015

(65) Prior Publication Data
US 2016/0249957 A1  Sep. 1, 2016

(30) Foreign Application Priority Data
Jul. 15, 2013  (FR) .................................... 13 56963

(51) Int. Cl.
*A61B 17/70*  (2006.01)

(52) U.S. Cl.
CPC ........ *A61B 17/7053* (2013.01); *A61B 17/707* (2013.01); *A61B 17/7049* (2013.01); *A61B 17/7067* (2013.01)

(58) Field of Classification Search
CPC ............ A61B 17/7049; A61B 17/7053; A61B 17/7067; A61B 17/707

(Continued)

(56) References Cited

U.S. PATENT DOCUMENTS 5,800,548 A * 9/1998 Martin ............... A61B 17/7049
606/250
5,899,903 A  5/1999 Cotrel (Continued)

FOREIGN PATENT DOCUMENTS

| EP | 2047813 A1 | 4/2009 |
|---|---|---|
| EP | 2609882 A1 | 7/2013 |
| FR | 2750033 A1 | 12/1997 |

OTHER PUBLICATIONS

PCT Written Opinion of the International Searching Authority dated Jan. 28, 2016, PCT Application No. PCT/FR2014/051801, 8 pages (including the English Translation).

*Primary Examiner* — Pedro Philogene
*Assistant Examiner* — David C Comstock
(74) *Attorney, Agent, or Firm* — MH2 Technology Law Group, LLP (57) ABSTRACT

The present invention relates to an implantable device (40), in particular to correct at least one vertebral level, comprising a rod having an outer radius (Rt) and a circumference determined at an area on a length (Lt); an elongate flat ligament; and a securing devices (50) of said elongate element in a partial encasing position of said area comprising first (51) and second (52) forks first general partly annular shape of inner radius, respectively, and comprising partly annular lower bearing surfaces respectively delimiting first (51*b*) and second (52*b*) circumference portions greater than half the circumference. Said securing devices (50) further comprises a shoulder part arranged relative to said lower bearing surfaces (51*a*, 52*a*) of the first and second forks (51, 52) so as to form a passage for said elongate element in said encasing position between said forks (51, 52) and said shoulder part (60).

14 Claims, 10 Drawing Sheets

(58) Field of Classification Search
USPC .......................................................... 606/263
See application file for complete search history.

(56) References Cited

U.S. PATENT DOCUMENTS

| | | | | |
|---|---|---|---|---|
| 7,833,248 | B2* | 11/2010 | Markworth | A61B 17/7049 403/64 |
| 7,842,071 | B2* | 11/2010 | Hawkes | A61B 17/7052 606/252 |
| 8,337,532 | B1* | 12/2012 | McLean | A61B 17/7011 606/279 |
| 9,101,460 | B2 | 8/2015 | Euteneuer et al. | |
| 9,675,386 | B2* | 6/2017 | Akbarnia | A61B 17/7053 |
| 2003/0220642 | A1* | 11/2003 | Freudiger | A61B 17/7005 606/254 |
| 2004/0049188 | A1* | 3/2004 | Slivka | A61B 17/7052 606/249 |
| 2005/0240180 | A1* | 10/2005 | Vienney | A61B 17/7032 606/246 |
| 2006/0025768 | A1* | 2/2006 | Iott | A61B 17/7032 606/86 A |
| 2009/0099604 | A1* | 4/2009 | Cho | A61B 17/7049 606/250 |
| 2012/0271354 | A1* | 10/2012 | Baccelli | A61B 17/7053 606/263 |
| 2013/0023878 | A1* | 1/2013 | Belliard | A61B 17/7053 606/74 |
| 2014/0257400 | A1* | 9/2014 | George | A61B 17/7049 606/278 |
| 2016/0183985 | A1* | 6/2016 | Campbell | A61B 17/7049 606/278 |
| 2017/0086889 | A1* | 3/2017 | Padilla | A61B 17/7053 |

* cited by examiner

IMPLANTABLE DEVICE, IN PARTICULAR FOR CORRECTING AT LEAST ONE VERTEBRAL LEVEL

BACKGROUND OF THE INVENTION

The present invention concerns the technical field of implantable devices, in particular to correct at least one vertebral level, optionally with fusion of said level, said devices comprising a rod, a flat elongate element and a device to secure said elongate element to said rod.

The rods are usually used in combination with an implant to correct at least one vertebral level, such as a screw and/or hook to receive said rod.

Said rods can be used in the treatment of scoliosis or for the treatment of degenerative pathologies. Different levels of degeneration are encountered e.g. at one vertebral level such as intervertebral disk disease or at two vertebral levels such as spondylolisthesis or several levels such as C- or S-scoliosis.

In these treatments the rod can be placed in contact with the vertebral level to be corrected via an elongate element which passes around at least one portion of a vertebral body and around said rod, and the ends of said elongate element can be held in place by a suture, knot or implantable securing device. Said securing device may for example comprise a housing to receive the rod and the elongate element wrapped around the rod, and clasping device to lock said rod and said elongate element in said housing. In general, the clasping device comprises a device to clamp said elongate element to prevent any movement thereof.

The disadvantage of clamping said elongate element is that it may generate early wear of said elongate element via abrasion, said elongate element generally being formed of fabric.

A further disadvantage of this securing device is that it does not allow adjustment of tensioning of the elongate element once the implantable device has been implanted at the vertebral level to be corrected since the elongate element is fully locked in place by the clamping device. Yet it is often necessary to adjust the correction provided by the rod that is linked to the elongate element, once the device has been positioned on the vertebral level to be corrected.

In addition, this type of device to secure an elongate element onto the rod is not easily reversible. It is most complex to unscrew the multiple screws to adjust correction at the vertebral level to be treated.

There is therefore a need for an implantable device, in particular to correct a vertebral level, comprising an elongate element and a device to secure said elongate element in a position encasing said rod allowing said elongate element to be tensioned around the rod once it has been secured in said encompassing position, without separating the securing device from the rod already positioned on a least one vertebral level to be corrected.

There is also a need for securing device that are easy to position and reposition.

SUBJECT AND SUMMARY OF THE INVENTION

According to a first aspect the subject of the invention is therefore an implantable device, in particular to correct at least one vertebral level optionally with fusion of said level, comprising:
  a. a rod having an outer radius (Rt) and a circumference (Ct) determined at an area (z) along its length ($L_t$);
  b. a flat elongate element; and
  c. a device to secure said elongate element in a position partly encasing said area (z).

Advantageously, said securing device comprises a first fork and second fork having a first general partly annular shape of inner radius ri1 and ri2 respectively. Said first and second forks comprise partly annular lower bearing surfaces respectively delimiting first and second circumference portions greater than one half of the circumference (Ct). Said securing device comprises a shoulder part arranged relative to said lower bearing surfaces of the first and second forks so as to form a passage for said elongate element in said encasing position between said forks and said shoulder part. The first and second forks and their inner radii ri1 and ri2 are determined in relation to the outer radius Rt of the rod so that the press-fitting of the first and second forks either side of the elongate element partly encasing said rod generates their deformation for securing thereof to said rod.

Advantageously, the securing device of the invention allows the elongate element to be tensioned in said encasing position since the elongate element is able to move in rotation around the rod between said forks and the shoulder part. The elongate element is simply locked in translation along the longitudinal axis (Lt) of the rod between said forks.

The practitioner is therefore able to adjust correction at the vertebral level to be treated even if the implantable device of the invention is positioned on at least one vertebral level to be corrected.

Advantageously the securing device comprises first and second forks deformable under the pressure applied by the rod when positioned in said forks, since said forks slightly retract and conform to the outer diameter Dt of the rod whilst maintaining (so-called elastic) deformation.

Advantageously the securing device of the invention achieves securing by clipping the forks onto the rod at a determined point arranged along the length thereof and called an area (z). The securing device is very easily detached by applying a traction force manually or using a tool to disengage the forks from the rod, this gives rise to deformation of the forks and removal thereof in their initial position corresponding to the inner radii ri1 and ri2.

During procedure, since the elongate element applies a traction force in a direction opposite the direction in which disengaging traction force must be applied, the securing device is fully secured to the rod. This latter provision provides additional security for the practitioner, the implantable device of the invention being intended to be implanted on the spine.

In the meaning of the invention by shoulder part is meant any connecting device ensuring a link between the first and second forks and spacing apart said first and second forks by a distance equal to or greater than the width of the flat elongate element, more preferably equal to or greater than the outer diameter Dt of the rod.

During procedure, the practitioner places the first and second forks either side of the elongate element arranged in an encasing position around said rod in an area (z), by clipping said forks onto the rod so that they deform and can be secured to the rod, their inner radii at the time of positioning being larger than or equal to the outer radius Rt of the rod.

The deformability of the first and second forks and their securing to said rod so that there is neither translation nor rotation of said forks on the rod are dependent on the following parameters: width of the cross-sections of said forks, the constituent material(s) of said forks, the inner radii ri1 and ri2 determined in relation to the outer radius Rt; the first and second circumferential portions of the annular lower bearing surfaces determined in relation to the circumference Ct of the rod so that said forks sufficiently encase the rod.

It is within the reach of the person skilled in the art to determine the widths of the cross-sections of the forks, and the material(s) for fabrication thereof so as to impart some deformability thereto (in particular to remain within an elastic deformation range when applying force to engage the rod in the securing device) and memory of their initial shape when at rest corresponding to the inner radii ri1 and ri2.

The inner radii ri1 and ri2 at rest of said forks are determined in relation to the outer radius Rt of the rod so that once the forks are secured to the rod they are unable to be moved either in translation or rotation thereupon. Preferably the inner radii ri1 and ri2 at rest of said forks are equal to or smaller than the outer radius Rt of the rod, preferably 3% smaller or equal to the outer radius Rt of the rod, more preferably 1% smaller or equal to the outer radius Rt of the rod, further preferably 0.7% smaller or equal to the outer radius of the rod.

The elongate element of the invention is preferably a fabric element which may be a braid, knit or woven, preferably a braid.

The elongate element comprises first and second ends.

The implantable device of the invention may also comprise a device with fastening loop such as described in patent application EP 2.555.698 A1 by the applicant, the loop device allowing securing together of the ends of the elongate element.

Preferably, the device with fastening loop comprises a rigid support comprising two side parts mounted between front and back parts, said first end being secured or able to be secured to said back part and said second end remaining free.

The device with fastening loop also comprises a locking element slidingly mounted on said side parts and delimiting front and back passage areas respectively with the front and back parts allowing said second free end to be passed through the back passage area and then the front passage area partly surrounding said locking element so that the portion of said elongate element extending substantially between its first end and the locking element forms a loop of given perimeter (p), and so that the application of opposite tension forces on the inner walls of the loop cause the movement of said locking element towards said front part and locking of the portion of elongate element in the front passage area between said locking element and the front part of the support.

It is also possible to secure together the first and second ends of the elongate element via a suture, knot or collapsible metal ring.

Preferably the inner distance (di) separating the side parts is in the order of the size of the main width (l) of said elongate element or shorter.

The implantable device of the invention can be used for the treatment of scoliosis or the treatment of degenerative pathologies, in particular for the treatment of different levels of degeneration e.g. at one vertebral level such as intervertebral disc disease or at two vertebral levels such as spondylolisthesis or several levels e.g. C- or S-scoliosis.

The elongate element of the invention passes around at least one portion of a vertebral body for example around a "lamina process" or vertebral lamina, or around a transverse process and/or crosses around both processes.

In one variant, said shoulder part is recessed in relation to said lower bearing surfaces, respectively by a distance h1 and h2 so as to form a passage for said elongate element.

Depending on height h1 and h2, the elongate element may or may not be pushed flat against the rod by the shoulder part, preferably the heights h1 and h2 are greater than the thickness (e) of the elongate element so as to impart some freedom of movement to said elongate element in rotation about the rod.

The minimum distance separating the first fork from the second fork, substantially corresponding to the minimum inner width of the shoulder part, combined with heights h1 and h2 such as defined above advantageously allows a space to be provided for the passing of a flat elongate element when said securing device is secured onto the rod. In particular, the distance separating the first fork from the second fork is equal to or greater than the outer diameter Dt of the rod so as to allow passing of the diameter of the rod when placing the first and second forks on the rod requiring 90° pivoting by said forks.

In one variant, the securing device comprises a piece having a lower bearing surface capable of receiving at least one portion of said elongate element, and clamping device that can be actuated in translation and arranged relative to said lower bearing surface so that the movement in translation of said clamping device allows the clamping of at least one portion of said elongate element against said lower bearing surface.

Advantageously the elongate element is not clamped directly on the rod but on a lower bearing surface, preferably substantially planar, via the clamping device. The friction area between the flat elongate element and the lower bearing surface is advantageously larger than if the elongate element had been clamped at one point, which device that clamping and hence securing of a portion of the elongate element against said lower surface is improved without being abraded and hence without deteriorating said portion of elongate element.

In a sub-variant, said piece comprises at least one region arranged so that it acts as first attaching members capable of cooperating with second attaching members supported by a grasping instrument e.g. an ancillary, said instrument assisting press-fitting of the forks onto the rod.

In one variant, the shoulder part spaces the first fork apart from the second fork by a distance equal to or greater than the width of said flat elongate element, in particular equal to or greater than the outer diameter Dt of the rod.

In one variant, the piece comprises a tapped hole and the clamping device comprises a screw having a threaded portion capable of cooperating with said tapped hole. Said clamping device also comprises a plate and connecting device ensuring a link between said screw and the plate and arranged so that when said screw is set in rotation it causes the movement in translation of said plate to clamp at least one portion of said flat elongate element against the lower bearing surface.

Advantageously, two portions of said elongate element can be clamped between the plate and the lower bearing surface. The plate is of substantially flat shape so that said at least one portion of said elongate element is clamped between the lower bearing surface and the plate which are two substantially planar surfaces therefore providing a large friction surface area. The contact surface between said at least one portion of said elongate element with the lower bearing surface and the plate being improved, clamping force is thereby increased. In addition, said at least one portion of said elongate element does not risk being deteriorated by pinching. Risk of wear and hence of early rupture of said elongate element are therefore prevented.

Preferably the screw at its distal end comprises an imprint able to cooperate with a matching imprint on a grasping instrument so that it can be set in rotation, in particular the imprint is of polygonal shape in particular six-lobed.

In one variant, the screw at its proximal end comprises a housing and the connecting device comprises at least one deformable portion able to be deformed so that it can be inserted in said housing and to return to its non-deformed shape so that it can be secured to said housing.

Advantageously, said at least one deformable portion is deformed for insertion thereof into said housing. In the non-deformed state, said position is secured to said housing by locking within the latter, in particular said portion abuts different regions of the housing depending on whether the screw is screwed or unscrewed in said tapped hole.

Therefore, when the screw and hence said housing are set in rotation, the housing rotates around said deformable portion and comes to abut this portion causing movement in translation thereof, and correlatively the movement in translation of the plate since the connecting device and hence said at least one deformable portion are linked to said plate.

In one variant said plate comprises a first surface and second surface that are substantially planar and opposite-lying, said second surface being oriented towards said lower bearing surface and said first surface being oriented towards the screw.

In one variant, the connecting device comprises at least two deformable portions, more preferably at least four deformable portions. In particular said deformable portions form a deformable T-shape.

In one variant the connecting device is secured to said plate.

The connecting device is preferably secured to the first surface of the plate, in particular the deformable T-shape portion projects from said first surface in the direction of the screw.

In one variant the piece is of parallelepiped shape, rectangular parallelepiped in particular, having side surfaces and preferably opposite upper and lower surfaces, said first and second forks projecting along a first side surface selected from among said side surfaces of the piece.

In one sub-variant, the piece comprises an opening arranged in one of its side surfaces acting as said attachment members. Preferably said opening is of oblong shape. Preferably said piece comprises two openings, each of said openings being arranged in one of its side surfaces, said two side surfaces lying opposite one another.

Preferably said piece is of rectangular or square parallelepiped shape, in particular cube-shaped.

In one variant, the shoulder part is the upper surface of said piece.

In one variant, the piece having an inner volume comprises an inlet orifice and outlet orifice in its inner volume for said elongate element so as to form a passage opening onto at least a clamping area partly delimited by said plate and the lower bearing surface.

In one variant, the first and second forks are in opposition.

In particular, the first and second forks are open one on the other so that they rotate by an angle of 90° when clipped onto the rod.

This provision prevents any risk of early detaching of the first and second forks from the rod during procedure since the force required to detach the first fork from the rod is applied in a direction opposite the direction required to detach the second fork from the rod.

In addition, the elongate element can encase the rod in a direction that may or may not be perpendicular to the longitudinal direction of the rod, which provides the practitioner with greater possibility for the arranging of the elongate element around at least one portion of a vertebral body.

With this arrangement it is possible to prevent the elongate element from mounting upon one of the forks but remains properly positioned between the two forks or abutting against one thereof.

In one variant of embodiment, the first and second forks comprise first and second ends, and the distance between the first ends and the distance between the second ends of the first and second forks is equal to or greater than the width (l) of the flat elongate element.

In one variant of embodiment, the shoulder part comprises a tapped hole able to cooperate with an instrument provided with a corresponding threaded portion.

It is possible to engage and disengage the securing device on the rod by mean of said instrument making use of said tapped hole.

In one variant of embodiment, the first and second forks lie in parallel planes.

Optionally, the elongate element therefore surrounds the rod being substantially perpendicular to the longitudinal direction (Lt) of the rod.

In one variant of embodiment, the first and second forks lie in secant planes, preferably forming an alpha angle of 45° or smaller, preferably 30° or smaller.

Advantageously, depending on the width of the lamina or of the "lamina process", the elongate element is not wound in a direction perfectly perpendicular to the longitudinal direction (Lt) of the rod. It is possible for the elongate element to be placed sideways on the rod. With this provision it is possible to prevent the elongate element from mounting upon one of the forks but remains properly positioned between the two forks or in abutment against one thereof.

In addition, with this provision it is possible to arrange two bearing points on the front branches of the first and second forks which are not in line with the two bearing points arranged at the rear branches of said forks, thereby improving stability and retaining of the securing device on the rod.

In one variant of embodiment, the implantable device of the invention comprises auxiliary retaining device to retain the securing device secured to said area (z) of said rod.

This arrangement may be necessary if additional security is desired by the practitioner to avoid any risk of decoapting of the securing device from the rod.

In one sub-variant of embodiment, said device comprises a screw having a threaded portion and said auxiliary retaining device has a general inverted U-shape comprising a base having an auxiliary opening from which first and second branches protrude transversely provided at their ends with concave bearing areas, said auxiliary device being arranged so that during procedure the first and second branches are positioned either side of the first and second forks, said auxiliary opening lying opposite said tapped hole, said concave bearing areas bearing upon the length of said rod, said threaded portion being passed through said opening and engaged with said tapped hole.

The auxiliary retaining device therefore applies pressure on the shoulder part of the securing device via their base, this pressure being applied in a direction opposite the direction in which pressure can be applied to disengage the securing device.

The pressure applied by the auxiliary retaining device is therefore distributed over the base thereof and on the concave bearing areas bearing upon the rod either side of the first and second forks.

Preferably the concave bearing areas bear upon the rod in a region in which the first and second forks do not cover the rod.

In one variant of embodiment, the screw comprises a shoulder which when being placed in position abuts the base of said auxiliary retaining device.

Advantageously, depending on the heights of the threaded portion and the shoulder of the screw, the elongate element may or may not be compressed by the free end of the screw. Preferably, the heights of the threaded portion and shoulder are determined so as not to compress the elongate element and thereby prevent any risk of degradation via pinching and abrasion.

Optionally the free end of the screw can be arranged in relation to the screw so that it is not driven in rotation when the screw is screwed into the tapped hole arranged in the shoulder part of the securing device. With this arrangement it is possible simply to apply pressure on the elongate element without rotation thereof which limits the risk of deteriorating said elongate element.

Preferably the free end of the screw is flat.

The auxiliary opening of the auxiliary retaining device may optionally be tapped so as to cooperate with the threaded portion of the screw. In this case, the threaded portion is separated from the shoulder by a groove, the groove being recessed in relation to the shoulder and the threaded portion. With this arrangement it is possible to engage the auxiliary retaining device with the screw, the auxiliary retaining device being locked at the groove between the shoulder and the threaded portion. During procedure, the practitioner therefore screws the threaded portion of the screw in the tapped hole of the shoulder part of the securing device without setting the auxiliary retaining device in rotation.

In one variant of embodiment, the first and second branches of said auxiliary retaining device lie in secant planes forming a beta angle, the beta angle preferably being 30° or smaller, preferably equal to alpha.

The first and second branches could also lie in substantially parallel planes, in particular if the first and second forks also lie in substantially parallel planes.

In one variant of embodiment, said securing device and optionally the auxiliary retaining device is in one or more materials selected from the list comprising: titanium, stainless steel, titanium and nickel alloy, polyetheretherketone (PEEK), PEK (polyetherketone), chromium cobalt, polyamide 6-6, polyamide 6, ethylene polyterephthalate, and in particular any other material having so-called >30-day biocompatibility.

According to a second aspect the subject of the invention is a kit for implantable device comprising an implantable device according to any of the preceding variants of embodiment, and a tool to grasp said securing device comprising a bar provided at its end with first attaching members able to operate with second attaching members supported by said securing device.

In one sub-variant the first attaching members are a thread and the second attaching members are a tapped hole arranged in the shoulder part or comprised in the piece of the invention, and optionally tapping arranged in the auxiliary opening of the base of the auxiliary retaining device.

According to one alternative, said second attaching members are one or two openings arranged in one or two side surfaces of the above-described piece.

BRIEF DESCRIPTION OF THE DRAWINGS

The present invention will be better understood on reading an example of embodiment of a kit for implantable device of the invention, and a second example of an implantable device of the invention that are non-limiting and illustrated by the following Figures in which.

DETAILED DESCRIPTION OF THE INVENTION

Figure 1:
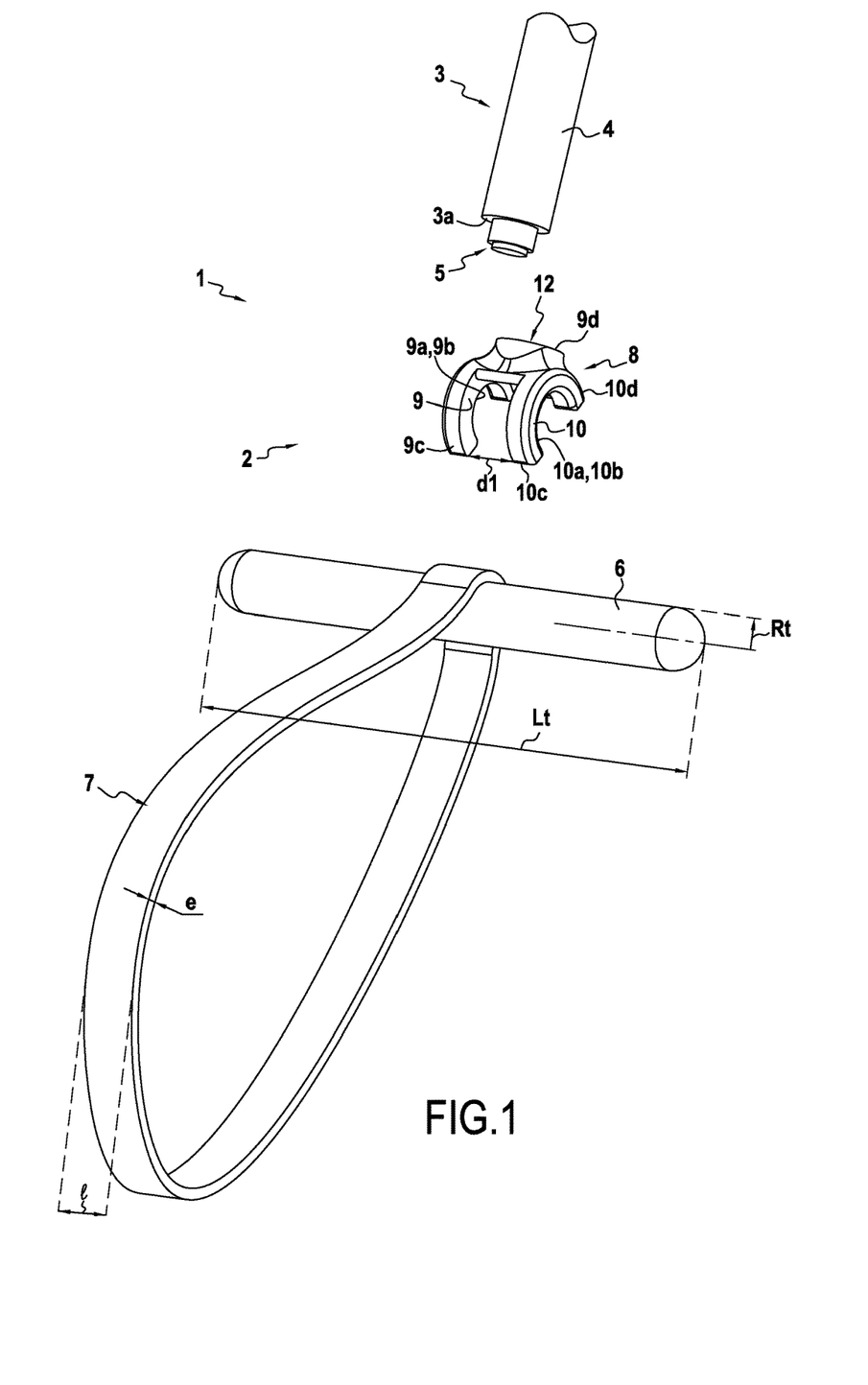
FIG. 1 is a perspective view schematically illustrating an example of a kit according to the invention comprising an example of an implantable device according to the invention.

Kit 1 for implantable device comprises an example of implantable device 2 and a grasping instrument 3 comprising a bar 4 provided at its end 3a with a thread 5.

Figure 2:
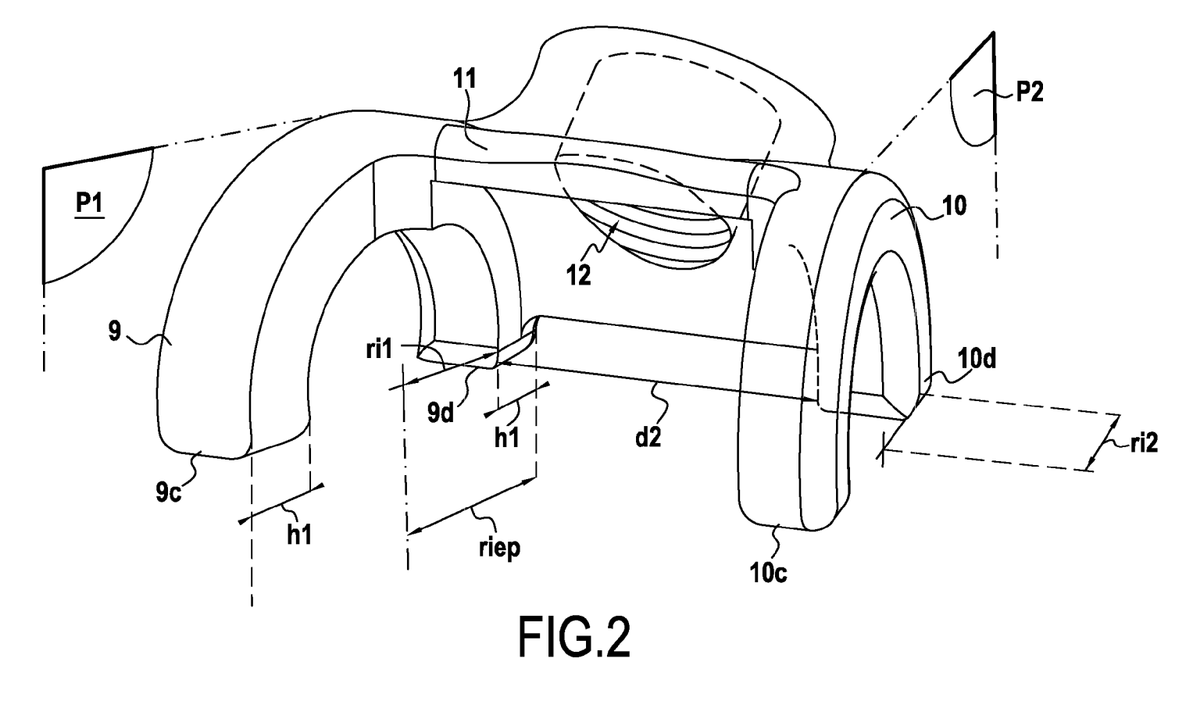
FIG. 2 is a perspective view schematically illustrating the securing device used in the implantable device illustrated in FIG. 1.

The implantable device 2 comprises a rod 6 having an outer radius Rt and a circumference Ct determined at an area z along its length; a flat elongate element 7; and a securing device 8 for said elongate element 7 in a position partly encasing said area z. Said securing device 8 comprises a first fork 9 and second fork 10 having a first general partly annular shape of inner radius ri1 and ri2 respectively. Said first 9 and second 10 forks comprise partly annular lower bearing surfaces 9a and 10a respectively delimiting first 9b and second 10b circumference portions greater than half the circumference Ct. Said securing device 8 comprises a shoulder part 11 having a second partly annular shape coaxial with said first partly annular shape, said second shape having an inner radius riep greater than the inner radii ri1 and ri2 by a distance h1 and h2 respectively so as to form a passage for said elongate element 7 in said encasing position between said forks 9 and 10 and said shoulder part 11. The first 9 and second 10 forks and their inner radii ri1 and ri2 are determined in relation to the outer radius Rt of the rod 6 so that the press-fitting of the first 9 and second 10 forks either side of the elongate element 7 partly encasing said rod 6, generates their deformation and then securing thereof to said rod 6.

It is also possible to place the securing device 8 manually on the rod 6 without the assistance of the grasping instrument 3.

The first 9 and 10 second forks comprise first 9c, 10c and second 9d, 10d ends, and the distance d1 between the first ends 9c, 10c and the distance d2 between the second ends 9d, 10d of the first 9 and second 10 forks are equal to or greater than the width l of the flat elongate element 7.

The shoulder part 11 comprises a tapped hole 12 capable of cooperating with the instrument 3 provided with a corresponding threaded end 3a.

In this specific example, the first fork 9 and the second fork 10 lie in parallel planes p1 and p2.

During procedure, the practitioner with the assistance of the instrument 3 causes the threaded end 3a to cooperate with the tapped hole 12 arranged in the shoulder part 11 so as to press-fit the first 9 and second 10 forks on the area z of the rod 6 thereby causing deformation thereof and then their securing onto the rod 6. The forks 9, 10 of the securing device 8 are placed either side of the elongate element 7 that is in a position encasing the rod 6. The securing device 8 therefore prevents any transverse movement of the elongate element 7 on the rod 6, i.e. any movement along the longitudinal axis Lt.

It is also possible to position the securing device 8 without the assistance of the instrument 3, simply manually.

In this specific example, the heights h1 and h2 are greater than the thickness e of the elongate element 7 so as to allow rotational movements of the elongate element 7 around the rod 6.

Figure 3:
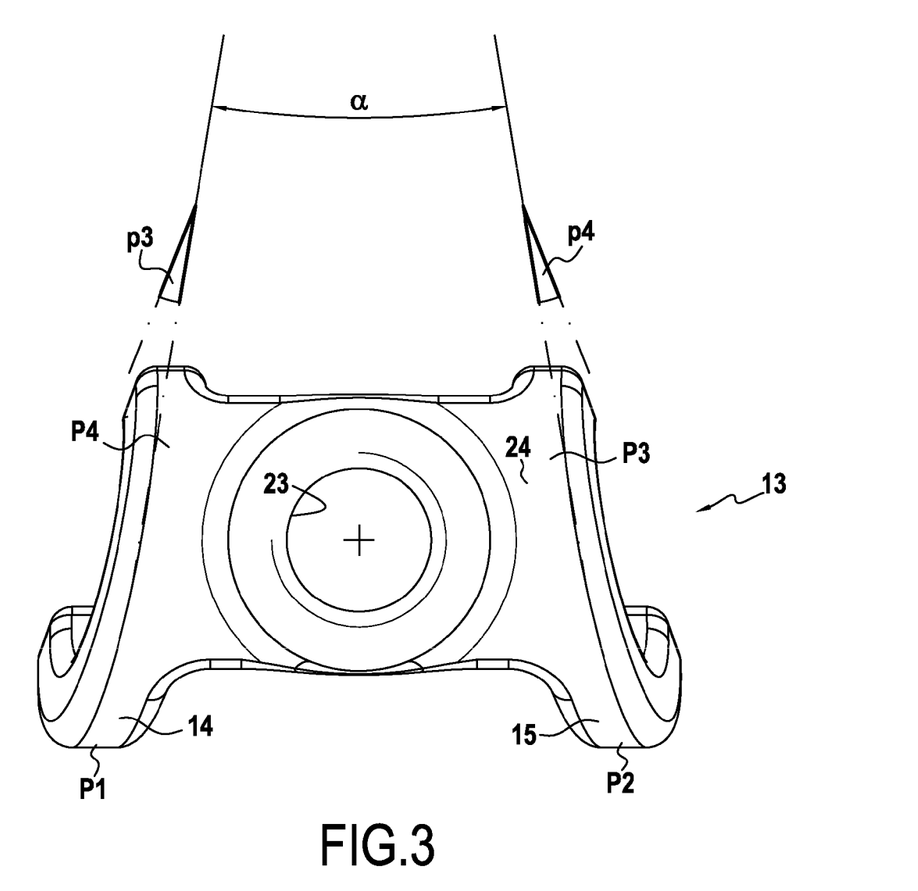
FIG. 3 is a perspective view schematically illustrating a variant of the securing device illustrated in FIG. 2.

FIG. 3 illustrates a variant 13 of the securing device 8 in which the first 14 and second 15 forks lie in secant planes p3 and p4 forming an alpha angle of 45° or smaller, preferably of 30° or smaller. The advantage of this arrangement is stabilising of the securing device 13 when they are positioned on the rod 6 since it develops at least four bearing points which are not in line with one another, respectively points P1, P2, P3 and P4. In addition, this arrangement prevents the elongate element 7 from overlapping the first 14 and second 15 forks when the elongate element 7 encases the rod 6 in a direction which is not substantially perpendicular to the axis Lt of the rod 6.

Figure 4:
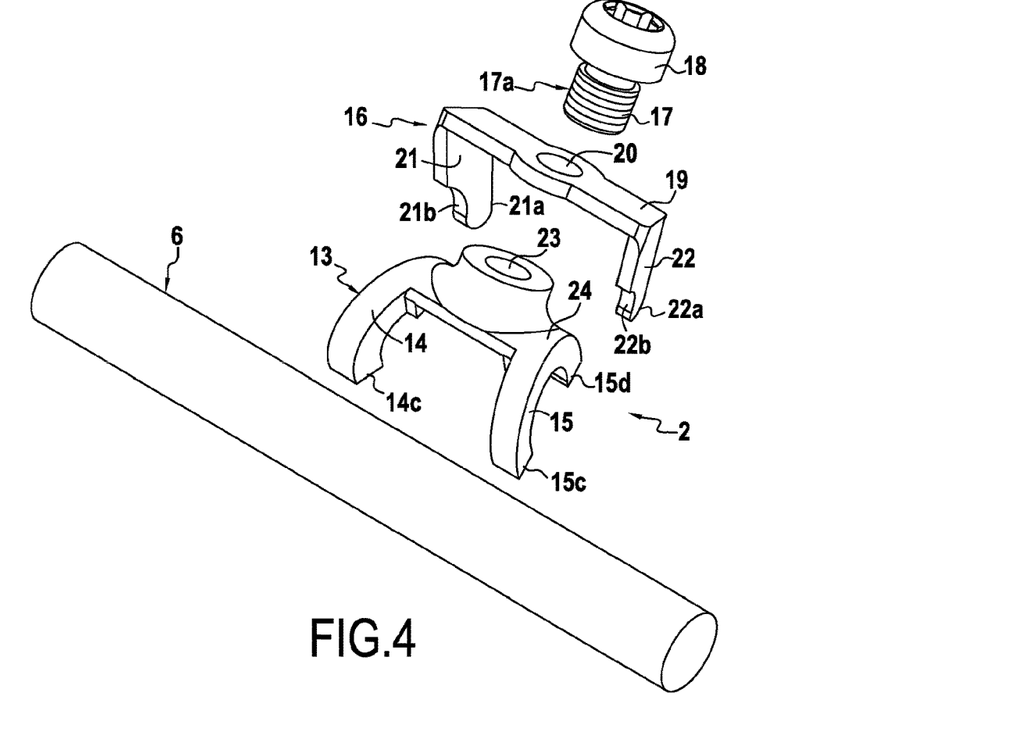
FIG. 4 is a perspective view schematically illustrating auxiliary retaining device in combination with the device illustrated in FIG. 1 and comprising the securing device illustrated in FIG. 3.
Figure 5:
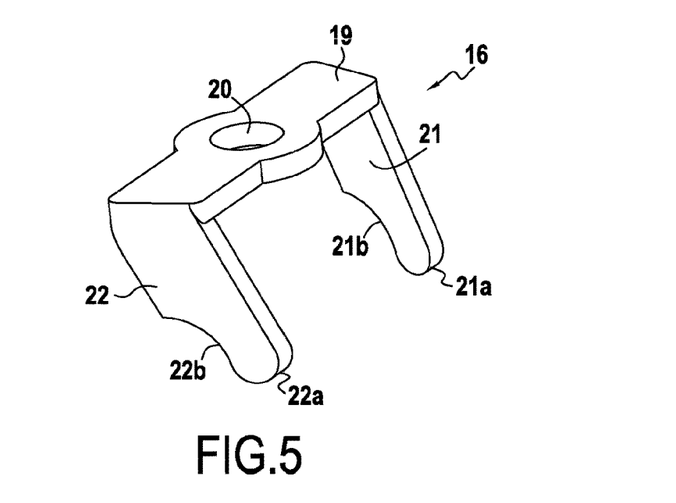
FIG. 5 is a perspective view schematically illustrating the auxiliary retaining device illustrated in FIG. 4.
Figure 6:
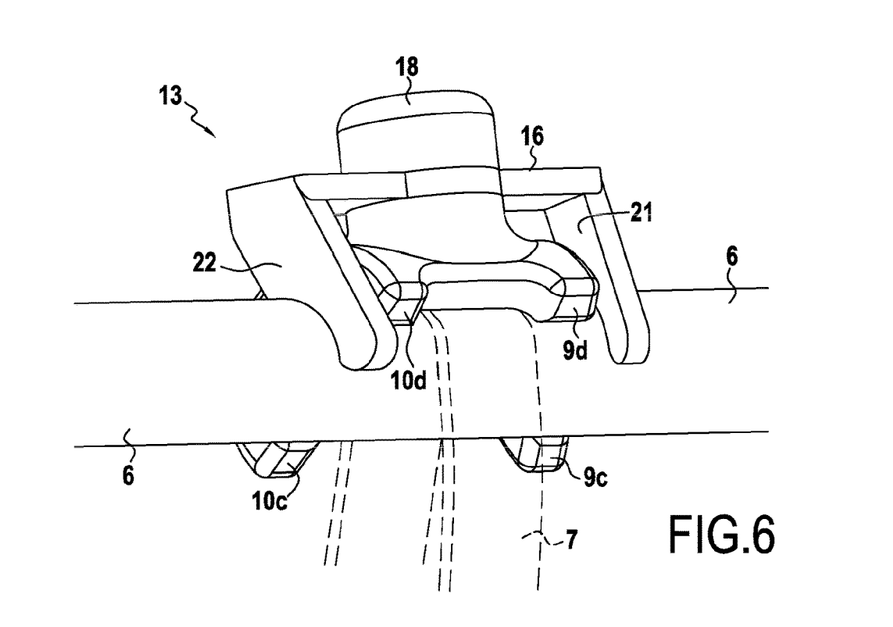
FIG. 6 is a schematic illustration in perspective of the example of implantable device according to the invention comprising the securing device illustrated in FIG. 3, a screw and the auxiliary retaining device illustrated in FIGS. 4 and 5.

The implantable device 2 may also comprise auxiliary retaining device 16 to retain the securing device 13 secured to said area z of said rod 6 such as illustrated in FIGS. 4 to 6.

The implantable device 2 also comprises a screw 17 having a threaded portion 17a and a shoulder 18. The auxiliary retaining device 16 is of general inverted U-shape comprising a base 19 having an auxiliary opening 20 from which project crosswise first 21 and second 22 branches provided along their ends 21a and 22a with concave bearing areas 21b and 22b. The auxiliary device 16 is arranged so that during procedure the first 21 and second 22 branches are positioned either side of the first 14 and second 15 forks, said auxiliary opening 20 lying opposite the tapped hole 23, said concave bearing areas 21b and 22b coming to bear upon the length of said rod 6. The threaded portion 17a of the screw 17 is then passed through the auxiliary opening 20 and engaged with said tapped hole 23 until the shoulder 18 comes to abut the shoulder part 24, in particular abutting the tapped hole 23 projecting in this specific example from the shoulder part 24. Depending on the height of the threaded portion 17a of the screw 17, the elongate element 7 passing between the forks 14 and 15 may or may not be gripped.

Preferably, the height of the threaded portion 17a of the screw 17 is determined so as not the grip the elongate element 7 allowing it to have possible rotational movement around the rod 6.

Figure 7:
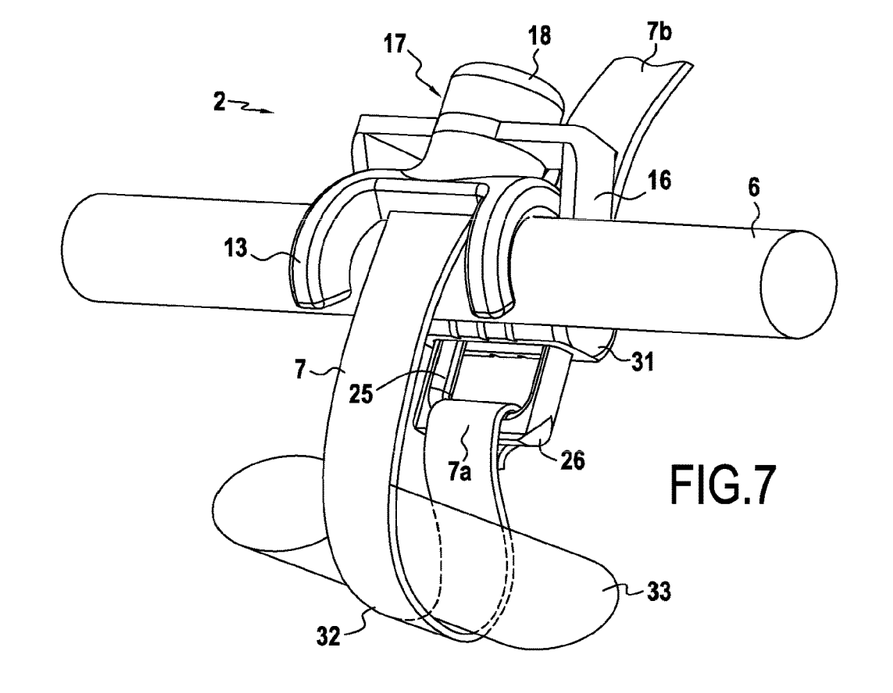
FIG. 7 is a schematic illustration in perspective giving an anterior view of the example of implantable device illustrated in FIG. 6 wherein the device further comprises a fastening loop device to fasten together the elongate element in said encasing position, the implantable device of the invention is illustrated in a position in which the elongate element passes around at least one portion of a vertebral body, around a "lamina process" in this specific example.
Figure 8:
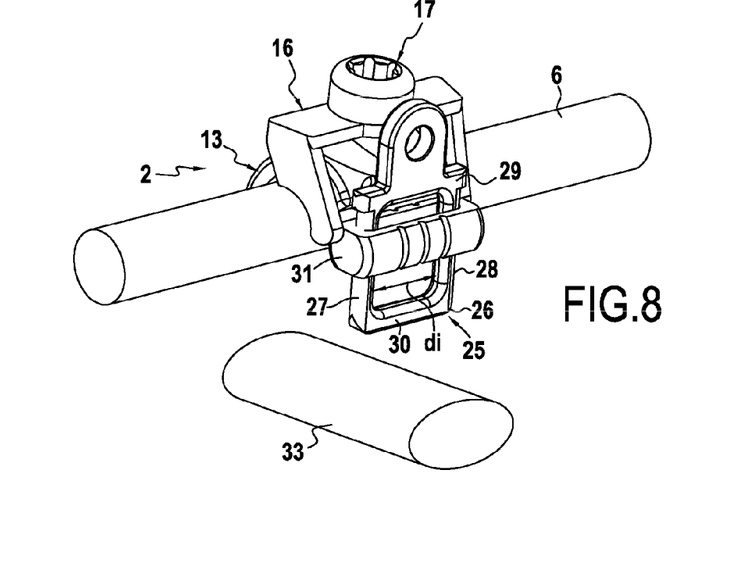
FIG. 8 is schematic illustration in perspective giving a posterior view of the device illustrated in FIG. 7.
Figure 9:
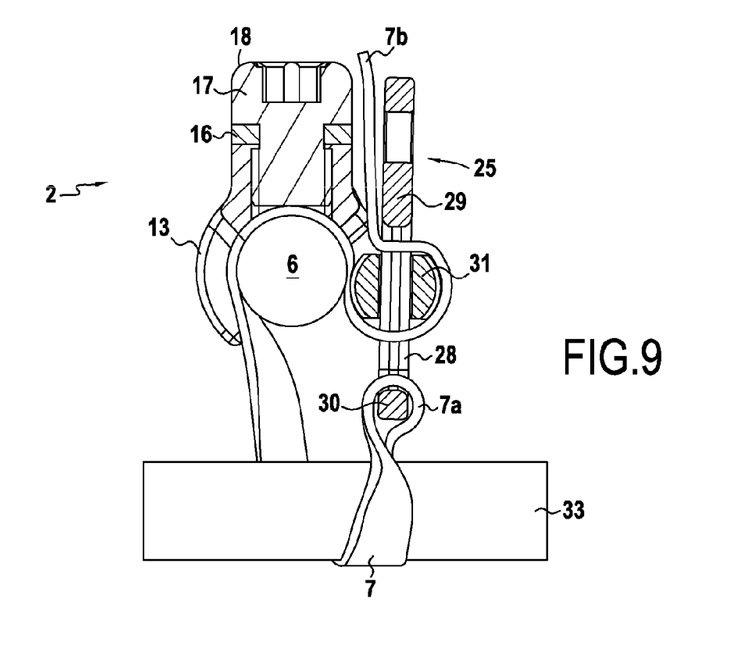
FIG. 9 is a schematic side-view illustration with cutaway parts of the device illustrated in FIGS. 7 and 8.

The implantable device 2 as illustrated in FIGS. 7 to 9, may also comprise a fastening loop device 25 as described in patent application EP 2.555.698 A1.

Preferably this fastening loop device 25 comprises a rigid support 26 having two side parts 27 and 28 mounted between front 29 and back 30 parts, the first end 7a of the elongate element 7 being secured or able to be secured to said back part 30 and the second end 7b of the elongate element 7 remaining free.

The fastening loop device 25 comprises a locking element 31 slidingly mounted on said side parts 27 and 28 and delimiting front and back passage areas with the front 29 and back 30 parts respectively allowing the passing of said free end 7b in the back passage area then the front passage area partly surrounding said locking element 31 so that the portion of said elongate element 7 substantially extending between its first end 7a and the locking element 31 forms a loop 32 of given perimeter p, and the applying of opposing tension forces on the inner walls of the loop 32 cases the movement of said locking element 31 towards said front part 29 and locking of the portion of elongate element 7 in the front passage area between said locking element 31 and the front part 29 of the support 26.

Preferably, the inner distance di separating the side parts 27 and 28 is in the order of the main width l of said elongate element 7.

The first 7a and second 7b ends of the elongate element 7 are secured together by device of the fastening loop device 25.

In FIGS. 7 and 9, the elongate element is in a position partly encasing the rod 6 and also passes around a portion of the vertebral body 33, in this specific example around a "lamina process". The elongate element 7 is not illustrated in FIG. 8 for simplification.

During procedure the practitioner can very easily adjust the tensioning of the elongate element 7; it is sufficient to unlock the locking element 31 and then to apply a tension force on the second free end 7b of the elongate element 7; the elongate element 7 then slides around the rod 6 between the forks 14 and 15 and shoulder part 24, without detaching the securing device 13. The practitioner then again locks the elongate element in rotation around the rod 6 via the locking element 31 causing it to slide towards the front part 29.

The inner radii of the first 9, 14 and second 10, 15 forks are determined in relation to the outer radius Rt of the rod 6 so that, once the securing device 8, 13 are clipped onto the rod 6, they are unable to move either in rotation or in translation along the longitudinal axis Lt of the rod 6.

In this specific example, the inner radii of the first 9, 14 and second 10,15 forks are 0.7% smaller than the outer radius Rt of the rod 6; preferably said inner radii are 2.73 mm and the outer radius Rt is 2.75 mm.

In this specific example, the width of the cross sections of the first ends 9c, 10c and 14c and 15c of the first 9, 14 and second 10, 15 forks is 1.50 mm, and the width of the cross-sections of the second ends 9d, 10d and 14d, 15d of the first 9, 14 and second 10, 15 forks is 2.00 mm.

The distance d1 separating the first ends 9c, 10c and 14c, 15c is 10 mm. The distance d2 separating the second ends 9d, 10d and 14d, 15d is 15 mm.

Preferably the securing device 8 or 16 are in titanium.

Figure 10:
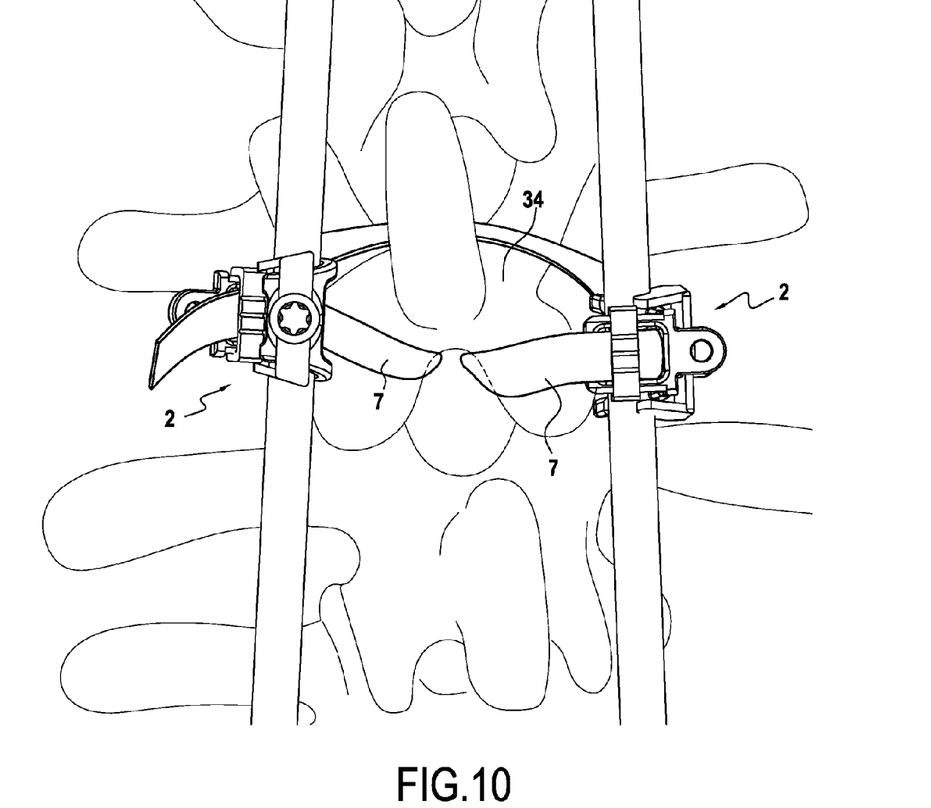
FIG. 10 is a schematic illustration giving a posterior view in which two implantable devices of the invention such as those illustrated in FIGS. 6 to 9 are positioned on at least one vertebral level to be corrected.

FIG. 10 illustrates two implantable devices 2 of the invention arranged on at least one vertebral level to be corrected.

The two elongate elements 7 are therefore passed around portions of a vertebral body 34, in this specific example around the "lamina processes".

Figure 11:
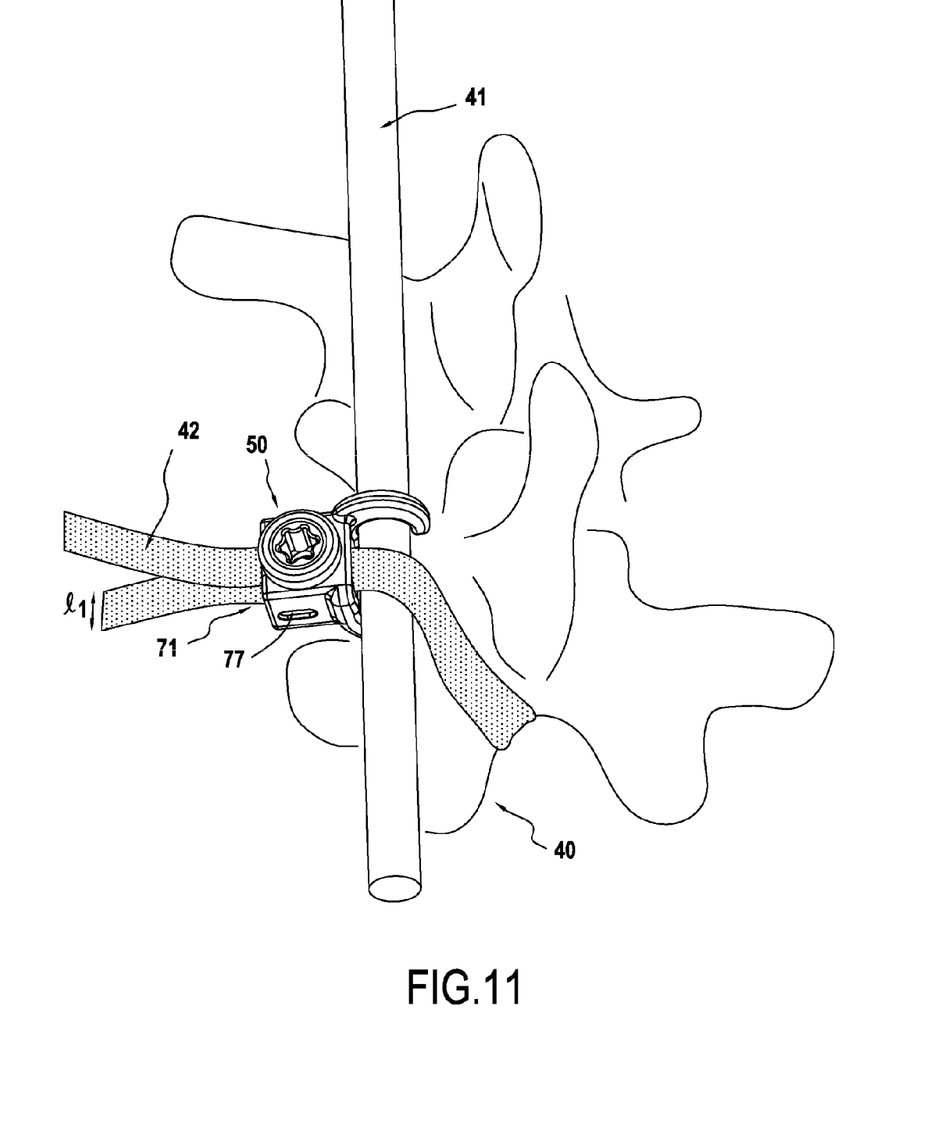
FIG. 11 is a schematic illustration in perspective of a second example of implantable device according to the invention positioned on at least one vertebral level to be corrected.

The implantable device 40 illustrated in FIG. 11 on at least one vertebral level to be corrected comprises a rod 41 having an outer radius Rt and a circumference Ct determined at an area z along its length; a flat elongate element 42; and a device 50 to secure said elongate element 42 in a position partly encasing said area z. Said securing device 50 comprises a first fork 51 and second fork 52 having a first general partly annular shape of inner radius ri1 and ri2 respectively. Said first 51 and second 52 forks comprise partly annular lower bearing surfaces 51a and 52a respectively delimiting first 51b and second 52b portions of circumference greater than one half of the circumference Ct. Said securing device 50 comprises a shoulder part 60 arranged in relation to said lower bearing surfaces 51a, 52a of the first and second forks 51, 52 so as to provide a passage for said elongate element 42 in said encasing position between said forks (51, 52) and said shoulder part 60. In particular, said shoulder part 60 is recessed in relation to said lower bearing surfaces 51a, 52a by a distance h1 and h2 respectively so as to form a passage for said elongate element 42. The first 51 and second 52 forks and their inner radii ri1 and ri2 are determined in relation to the outer radius Rt of the rod 42 so that the press fitting of the first 51 and second 52 forks either side of the elongate element 42 partly encasing said rod 41 generates their deformation for securing thereof on said rod 41.

The securing device 50 comprises a piece 70 having a lower bearing surface 71 capable of receiving at least one portion of said elongate element 42, and clamping device 80 that can be actuated in translation and arranged in relation to said lower bearing surface 71 so that the movement in translation of said clamping device 80 allows the clamping of at least one portion of said elongate element 42 against said lower bearing surface 71. As can be seen in FIG. 11, the elongate element 42 passes around at least one portion of a vertebral body after which its two free ends pass over the lower bearing surface 71 so that the two superimposed portions of said elongate element 42 are held together and clamped against said lower bearing surface 71 by the clamping device 80.

Figure 12:
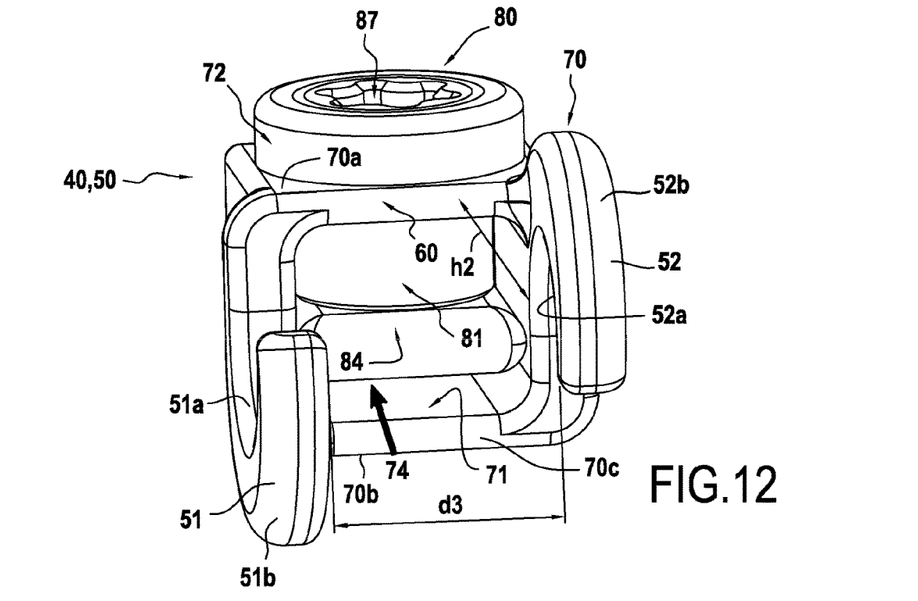
FIG. 12 is a schematic side view illustration of the securing device of the second example of implantable device illustrated in FIG. 11.
Figure 13:
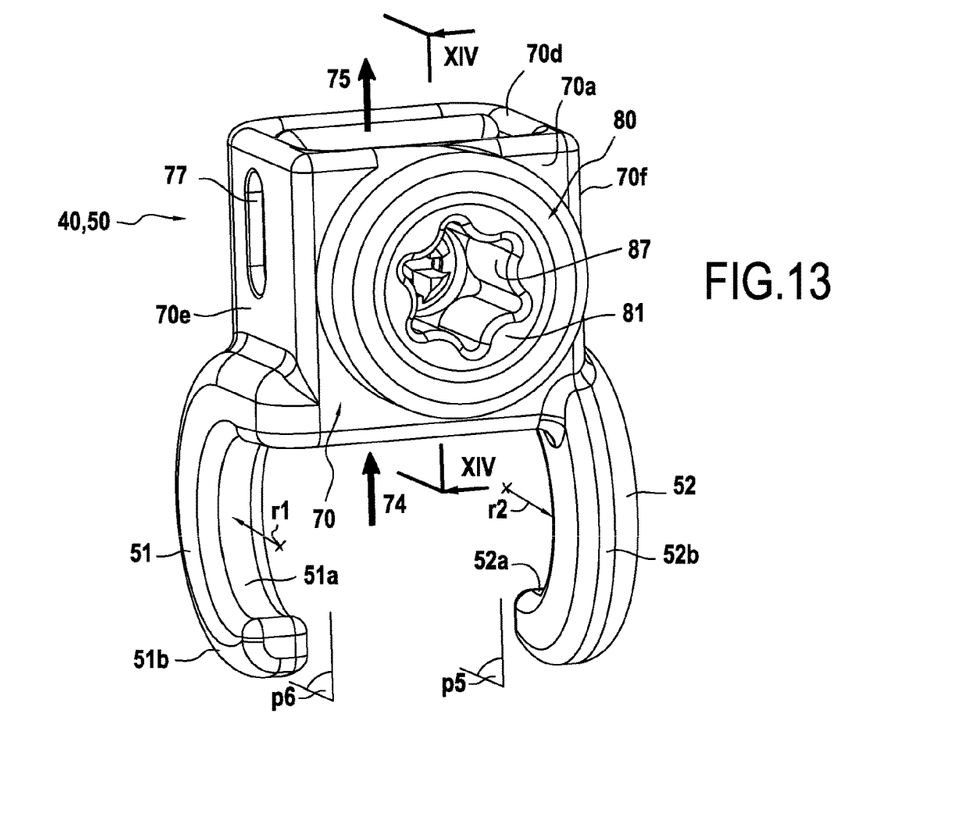
FIG. 13 is a schematic overhead illustration of the securing device of the second example of implantable device illustrated in FIG. 11.

The shoulder part 60 spaces apart the first 51 and second 52 forks by a distance d3 equal to or greater than the width ll of said flat elongate element 42 and equal to or greater than the diameter Dt of the rod 41 so that the forks 51,52 are able to pivot by 90° when being positioned on the rod 41.

Figure 14:
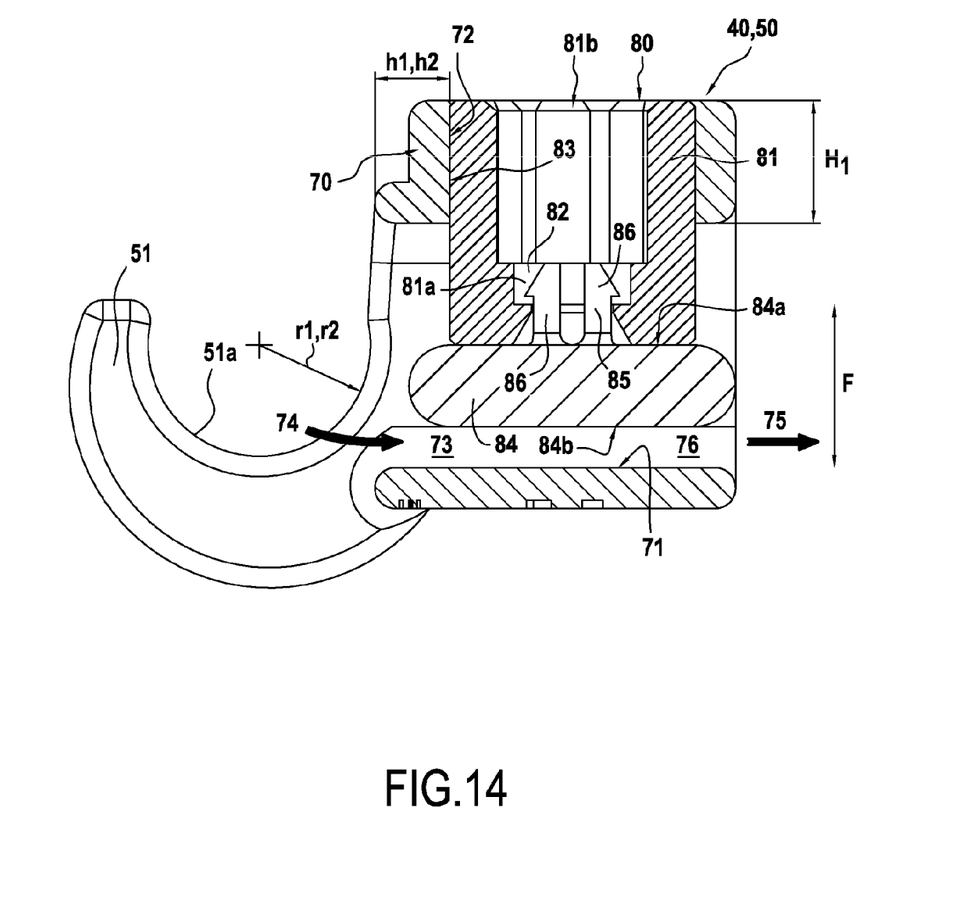
FIG. 14 is a schematic illustration of the securing device illustrated in FIGS. 11 to 13 along the sectional plane XIV-XIV in FIG. 13.

The piece 70 comprises a tapped hole 72, and the clamping device 80 comprises a screw 81 having a threaded portion 83 able to cooperate with said tapped hole 72 over height H1. The clamping device 80 also comprise a plate 84 and connecting device 85 ensuring a link between said screw 81 and the plate 84 and arranged so that the setting in rotation of said screw 81 causes the movement in translation along axis F of said plate 84 to clamp at least one portion of said elongate element 42 against the lower bearing surface 71. The plate 84 comprises a first surface 84a and a second surface 84b lying opposite and substantially planar. The screw 81 at its proximal end 81a comprises a housing 82 and at its distal end 81b an imprint 87, in particular a polygonal imprint particularly six-lobed capable of cooperating with the matching imprint of a grasping instrument to actuate the clamping device 80.

The connecting device 85 comprises at least one deformable portion 86 able to be deformed so that it can be inserted in said housing 82 and of returning to its non-deformed shape so that it can be secured to said housing 82. In this specific example, the connecting device 85 comprise four separate deformable portions 86 (only two of which are illustrated along the sectional plane XIV-XIV) forming a deformable T-shape. The connecting device 85 in this specific example is secured to the plate 84, in particular to its substantially planar first surface 84a.

The piece 70 in this specific example is of parallelepiped shape in particular a rectangular, especially square parallelepiped shape having side surfaces (70c, 70d, 70e, 70f), and upper 70a and lower 70b particularly opposite-lying surfaces, said first 51 and second 52 forks projecting along a first side surface 70c selected from among said side surfaces 70c, 70d, 70e, 70f of the piece 70. The shoulder part 60 is the upper surface 70a of said piece 70. The piece 70 having an inner volume 73 comprises an inlet orifice 74 and outlet orifice 75 in its inner volume 73 for said elongate element 42 so as to form a passage opening onto at least one clamping area 76 partly delimited by said plate 84 and the lower bearing surface 71.

The piece 70 comprises first attachment members 77 arranged in its side surfaces 70e and 70f, in particular two openings particularly of oblong shape, only the opening arranged in side surface 70e being illustrated in FIGS. 11 and 13. The second opening, which cannot be seen, is arranged inside surface 70f, opposite side surface 70e. The first attachment members 77 are able to cooperate with second attachment members (not illustrated) of a grasping instrument, said instrument providing assistance to position the securing device 50, and hence the forks 51, 52 on the rod 41.

The first 51 and second 52 forks lie opposite and in parallel planes p5, p6.

During procedure, once the elongate element 42 is positioned around at least one portion of a vertebral body and at least partly around the rod 41, the practitioner with the aid of an instrument provided with second attachment members cooperating with the first attachment members 77 press-fits the securing device 50 onto the rod 41 by pivoting the first 51 and second 52 forks by about 90° around the rod 41 thereby causing deformation thereof and then their securing onto the rod 41 at area z. The positioning of the securing device 50 can also be obtained manually by the practitioner.

In both cases, this operation causes deformation of the forks 51, 52 for securing thereof onto said rod 41. The practitioner then passes the free ends of the flat elongate element 42 into the clamping area 76 through the inlet orifice 74 and outlet orifice 75 and manually applies a tension force or using a suitable instrument on the free ends of the elongate element 42. Finally, the practitioner actuates the clamping device 80 via a grasping tool (not illustrated) provided with an imprint matching the imprint 87 arranged in the proximal part 81*b* of the screw 81 to set the screw 81 in rotation. The housing 82 then comes to abut the upper parts of said deformable portions 86 causing translation along axis F of the plate 84 drawing it close to the lower bearing surface 71 and thereby clamp the superimposed portions of the elongate element 42.

Advantageously the opposing arrangement of the first and second forks 51, 52 prevents any detachment of said forks 51, 52 from the rod 41. In addition, the arrangement of at least one portion of the elongate element 42, in this specific example of at least two portions of the elongate element 42 superimposed between the second substantially planar surface 84*b* of the plate 84 and the lower also substantially planar bearing surface 71, provides a large contact surface with the elongate element 42 and a very strong clamping force. For example, for a torque of 6 N.m (Newtons.meter) applied to the screw 81 via a grasping tool under the effect of a traction force of 1067 Newtons applied to the two free ends of the elongate element 42 inserted in the securing device 50, the elongate element 42 remains fully retained between the plate 84 and the lower bearing surface 71.

Finally, the forks 51, 52 of the securing device 50 are positioned either side of the elongate element 42 which is in encasing position around the rod 41. The securing device 50 therefore prevents any transverse displacement of the elongate element 42 on the rod 41, i.e. any movement along the longitudinal axis Lt.

The invention claimed is:

1. An implantable device, in particular to correct at least one vertebral level, optionally with fusion of said at least one vertebral level, comprising:
   a. a first rod having an outer radius Rt and a circumference Ct determined at an area z along its length Lt;
   b. a flat elongate fabric element;
   c. a device to secure said elongate element in a position partly wrapping said area z;
   wherein said securing device comprises a first fork having a first general partly annular shape of inner radius ri1 and defining a first vertical plane, and a second fork having a first general partly annular shape of inner radius ri2 and defining a second vertical plane, wherein the first vertical plane and the second vertical plane are spaced apart from each other,
   wherein said first fork comprises a partly annular lower bearing surface delimiting a first portion of circumference greater than one half of the circumference Ct, and said second fork comprises a partly annular lower bearing surface delimiting a second portion of circumference greater than one half of the circumference Ct,
   wherein said securing device comprises a shoulder part arranged relative to said lower bearing surfaces of the first and second forks so as to form a passage for said elongate element in said wrapping position between said first and second forks, and said shoulder part, and
   wherein the first and second forks and their inner radii ri1 and ri2 are determined in relation to the outer radius Rt of the first rod so that the press-fitting of the first and second forks on either side of the elongate element partly wrapping said first rod causes deformation of the first and second forks and then causes the first and second forks to be secured to said first rod.

2. The implantable device according to claim 1, wherein said shoulder part is recessed relative to said lower bearing surfaces, by a distance h1 and h2 respectively, so as to form a passage for said elongate element.

3. The implantable device according to claim 1, wherein the securing device comprises a piece having a lower bearing surface capable of receiving at least one portion of said elongate element, and clamping device which can be actuated in translation and arranged relative to said lower bearing surface so that the movement in translation of said clamping device allows the clamping of at least one portion of said elongate element against said lower bearing surface.

4. The implantable device according to claim 3, wherein the piece comprises a tapped hole, and the clamping device comprises a screw having a threaded portion able to cooperate with said tapped hole, and wherein said clamping device further comprises a plate and connecting device ensuring a link between said screw and the plate and arranged so that the setting in rotation of said screw causes the movement in translation of said plate to clamp at least one portion of said elongate element against the lower bearing surface.

5. The implantable device according to claim 4, wherein the screw at its proximal end comprises a housing and wherein the connecting device comprises at least one deformable portion able to be deformed so that it can be inserted in said housing and to recover its non-deformed shape for securing to said housing.

6. The implantable device according to claim 4, wherein the connecting device is secured to said plate.

7. The implantable device according to claim 3, wherein the piece is rectangular parallelepiped shape comprising side surfaces, and opposite-lying upper and lower surfaces, said first and second forks projecting along a first side surface selected from among said side surfaces of the piece.

8. The implantable device according to claim 7, wherein the shoulder part is the upper surface of said piece.

9. The implantable device according to claim 3, wherein the piece having an inner volume comprises an inlet orifice and an outlet orifice in its inner volume for said elongate element so as to form a passage opening onto at least one clamping area partly delimited by a plate and the lower bearing surface.

10. The implantable device according to claim 1, wherein the shoulder part spaces apart the first fork and the second fork by a distance equal to or greater than the width of said flat elongate element.

11. The implantable device according to claim 1, wherein the first and second forks are in opposition.

12. The implantable device according to claim 1, wherein the first and second forks lie in parallel planes.

13. The implantable device according to claim 1, wherein said securing device includes one or more materials selected from the list consisting of: titanium, stainless steel, a titanium and nickel alloy, polyetheretherketone (PEEK), PEK (polyetherketone), chromium cobalt, polyamide 6-6, polyamide 6, and ethylene polyterephthalate.

14. A kit for implantable device comprising an implantable device according to claim 1, and a grasping tool for said securing device comprising a bar provided at its end with first attaching members able to cooperate with second attaching members supported by said securing device.

* * * * *